(12) United States Patent
Malik et al.

(10) Patent No.: US 8,603,833 B2
(45) Date of Patent: Dec. 10, 2013

(54) GERMANIA-SILICA-BASED SOL-GEL MONOLITH AND USES THEREOF

(75) Inventors: Abdul Malik, Tampa, FL (US); Erica B. Turner, Tampa, FL (US); Scott S. Segro, Englewood, FL (US)

(73) Assignee: University of South Florida, Tampa, FL (US)

( * ) Notice: Subject to any disclaimer, the term of this patent is extended or adjusted under 35 U.S.C. 154(b) by 403 days.

(21) Appl. No.: 13/152,720

(22) Filed: Jun. 3, 2011

(65) Prior Publication Data

US 2012/0004434 A1 Jan. 5, 2012

Related U.S. Application Data

(60) Provisional application No. 61/351,120, filed on Jun. 3, 2010.

(51) Int. Cl.
 *B01D 15/26* (2006.01)
(52) U.S. Cl.
 USPC ........... 436/178; 210/635; 204/455; 204/605; 95/88; 96/101
(58) Field of Classification Search
 USPC ....... 436/178; 210/635; 204/455, 605; 95/88; 96/101
 See application file for complete search history.

(56) References Cited

U.S. PATENT DOCUMENTS

| | | | |
|---|---|---|---|
| 7,622,191 B2 | 11/2009 | Malik et al. | |
| 2003/0147606 A1* | 8/2003 | Wang et al. | 385/123 |
| 2007/0095736 A1 | 5/2007 | Malik et al. | |
| 2008/0223786 A1* | 9/2008 | Xu et al. | 210/656 |
| 2009/0008327 A1* | 1/2009 | Xu | 210/635 |

OTHER PUBLICATIONS

Heaney et al., "Solgel-derived photosensitive germanosilicate glass monoliths", Optics Letters, vol. 25, No. 24, Dec. 15, 2000, 1765-1767.*
Alonso, B. et al. "Structural Control in Germania Hybrid Organic—Inorganic Materials" *Chem. Mater.*, 2005, 17(12):3172-3180.
Que, W. et al. "Violet upconversion emission of sol-gel neodymium-doped $GeO_2$-$SiO_2$ thin films via organically modified silane precursors" *Journal of Crystal Growth*, 2006, 288:75-78.
Segro, S.S. et al. "Sol-Gel Germania Triblock Polymer Coatings of Exceptional pH Stability in Capillary Microextraction Online-Coupled to High-Performance Liquid Chromatography" *Analytical Chemistry*, May 15, 2010, 82(10):4107-4113.
Segro S.S. et al. "Ultra-high-stability, pH-resistant sol-gel titania poly(tetrahydrofuran) coating for capillary microextraction on-line coupled to high-performance liquid chromatography" *Journal of Chromatography A*, 2009, 1216:4329-4338.

(Continued)

*Primary Examiner* — Monique Cole
(74) *Attorney, Agent, or Firm* — Saliwanchik, Lloyd & Eisenschenk

(57) ABSTRACT

The present invention provides germania-silica-based sol-gel monoliths that form the solid-phase material for extraction, isolation, preconcentration, and separation of analytes. In one embodiment, the germania-silica-based sol-gel monolith can be used to coat surfaces of the inner walls of extraction and chromatographic columns. In a preferred embodiment, the sol-gel germania-silica monolith of the present invention is formed from hydrolysis and polycondensation of precursors comprising tetraethoxygermane, tetramethoxysilane, and polyethylene glycol. Also provided are methods of preparing the germania-silica-based sol-gel monolith of the present invention.

20 Claims, 13 Drawing Sheets

(56) References Cited

OTHER PUBLICATIONS

Li, X. et al. "pH-resistant titania hybrid organic-inorganic sol-gel coating for solid-phase microextraction of polar compounds" *Analytica Chimica Acta*, 2007, 590:26-33.

Liu, M. et al. "Preparation and characteristics of high pH-resistant sol-gel alumina-based hybrid organic-inorganic coating for solid-phase microextraction of polar compounds" *Journal of Chromatography A*, 2006, 1108:149-157.

Kulkarni, S. et al. "Sol-gel immobilized short-chain poly(ethylene glycol) coating for capillary microextraction of underivatized polar analytes" *Journal of Chromatography A*, 2007, 1174:50-62.

Alhooshani, K. et al. "Sol-gel approach to in situ creation of high pH-resistant surface-bonded organic-inorganic hybrid zirconia coating for capillary microextraction (in-tube SPME)" *Journal of Chromatography A*, 2005, 1062:1-14.

* cited by examiner

Where Y=condensation residue from PEG

GERMANIA-SILICA-BASED SOL-GEL MONOLITH AND USES THEREOF

CROSS-REFERENCE TO RELATED APPLICATION

The present application claims the benefit of U.S. Application Ser. No. 61/351,120, filed Jun. 3, 2010, which is herein incorporated by reference in its entirety.

FIELD OF INVENTION

This invention relates to chromatographic and extraction columns. In one embodiment, the invention discloses the construction and use of germania-silica-PEG-based monoliths.

BACKGROUND

In recent years, sol-gel chemistry has attracted considerable interest in chemical analysis, in part, to the ease of which inorganic-organic hybrid materials can be fabricated. Silica-based sol-gel materials have received the most attention. Silica-based coatings and monoliths have been synthesized via sol-gel processes and silica-based sol-gel stationary phases represent a rapidly growing area within separation science. The chemical properties of sol-gel materials can be fine-tuned via simple manipulation of ingredients and reactions that commonly take place at ambient temperatures. However, silica-based sol-gel materials also have many drawbacks, including their instability under extreme pHs and harsh solvents.

Other metal oxides, such as aluminum, titania, zirconia and hafnia, have been incorporated into silica-based systems; however, all of these hybrid materials have significant drawbacks. While titania and zirconia both exhibit enhanced mechanical strength and higher stability in extreme pHs in comparison to silica, they are both adsorptive and their surface chemistry differ significantly from that of silica (Winkler & Marme, *J Chromatogr. A.* 2000, 888, 51; Jiang & Zuo, *Anal. Chem.* 2001, 73, 686; Tani, & Suzuki, *J. Chromatogr. A.* 1996, 722, 129; Tsai, et al. *J. Chromatogr. B.* 1994, 657, 285; Fujimoto, *Electrophoresis.* 2002, 23, 2929).

Sol-gel titania-PDMS (Kim, et al. *J. Chromatogr. A.* 2004, 1047, 165) and sol-gel zirconia-PDMDPS (Alhooshani, et al. *J. Chromatogr. A.* 2005, 1062, 1) coatings fabricated by the present inventors showed stability under highly acidic and alkaline environments. These coatings also provided excellent solvent stability due to their ability to form direct chemical bonding with capillary inner walls. However, the use of titania and zirconia alkoxides as precursors of the silica-based sol-gel material also have significant disadvantages. For example, sol-gel titania/zirconia-silica materials have very rapid reaction rates, leading to instantaneous precipitation of zirconia when water is added to the system (Chang, et al. *J. Membr. Sci.* 1994, 91, 27). In addition, metal-bound hydroxyl groups on these zirconia and titania-based materials serve as adsorptive sites to polar solutes. This can cause problems such as sample loss, difficulty in reproducibility, sample carryover, peak distortion, and peak tailing (Alhooshani, et al. *J. Chromatogr. A.* 2005, 1062, 1). Narrow-bore zirconia monolithic columns were prepared by coating the silica surface with a layer of zirconia, followed by washing with dry ethanol and then water to promote hydrolization of zirconium ethoxide. Zirconia monolithic columns were also prepared by a sol-gel process with a solution of acetic acid catalyst, PEG and n-butanol (Randon, et *J. Chromatogr. A.* 2006, 1109, 19).

Hafnia lies within the same periodic group as titania and zirconia and has a high dielectric constant and good thermodynamic interfacial compatibility with silica. Hoth et al. (Hoth, et al. *J. Chromatogr. A.* 2005, 1079, 392-396) prepared metal oxide monoliths composed of $ZrO_2$ and $HfO_2$ via in situ synthesis. However, its disadvantages include problems of phase separation during annealing, especially at higher Hf concentrations. In $SiO_2$ sol gels, heat treatment leads to further condensation, thereby strengthening the silica network. The incorporation of Hf in silica networks leads to non-bonding oxygen, which suggests that $HfO_2$ phase separation occurs as temperature increases (O'Dell, et al. *Solid State Nuclear Magnetic Resonance.* 2008, 33, 16).

Alumina has also been incorporated into silica systems as it has many attractive qualities including excellent pH, thermal and mechanical stability. It also has a high surface area and is capable of ligand exchange, thereby capable of extracting polar compounds. Since alumina has Lewis acidity and basicity as well as a low concentration of Brønsted acid sites (Nawrocki, et al. *J. Chromatogr. A.* 2004, 1028, 1; Nawrocki, et al. *J. Chromatogr. A.* 2004, 1028, 31; Claessens & Van Sraten, *J. Chromatogr. A.* 2004, 1060, 23; Grün, et al. *J. Chromatogr. A.* 1996, 740, 1), it can undergo both ion and ligand exchange (Nawrocki, et al. *J. Chromatogr. A.* 2004, 1028, 1). Like zirconia, titania and hafnia, alumina also undergoes very fast reactions in the presence of water and has many adsorptive sites within alumina hydroxyl-terminated polydimethysiloxante (PDMS) coatings, which need to be deactivated (Liu, et al. *J. Chromatogr. A.* 2006, 1108, 149-157). Fujita et al. (Fujita, et al. *J. Non-Cryst. Solids.* 2008, 354, 659-664) developed $Cr^{3+}$-doped macroporous $Al_2O_3$ monoliths using the sol-gel method followed by phase separation. This new metal-salt derived method developed by Gash and coworkers enables the synthesis of metal oxide aerogels and xerogels from the corresponding metal salts (Gash, et al. *Chem. Mater.* 2001, 13, 999; Gash, et al. *Chem. Mater.* 2003, 15, 3268; Gash, et al. *J. Non-Cryst. Solids* 2001, 285, 22; Baumann, et al. *Chem. Mater.* 2005, 17, 395).

In the periodic table, germanium is a metalloid that lies within the same group as silicon, indicating that they share similarities in chemical structures and properties. Germania ($Ge-O_2$) has been shown to be an isostructural analog of silica ($Si-O_2$) (Fang, et al. *Anal. Chem.* 2007, 79, 9441-9451). Currently, germania is used in the optical fields for making waveguide films with controllable refractive index, photonic devices such as high-density optical data reading and storage devices, upconversion lasers, infrared laser viewers, and indicators (Chen, et al. *J. Non-Cryst. Solids.* 1994, 178, 135; Brusatin, et al. *J. Am. Ceram. Soc.* 1997, 80, 3139; Brede, et al. *Appl. Phy. Lett.* 2000, 63, 729; McFarlane, *J. Opt. Soc. Am. B.* (1993) 11, 871; Downing, et al. *Science.* 1996, 273, 1185; Maciel, et al. *Appl. Phys. Lett.* 2000, 76, 1978; Shigemura, et al. *J. Appl. Phys.* 1999, 85, 3413). Que et al. (Que, et al. *Journal of Crystal Growth.* 2006, 288, 75-78) fabricated $Nd^{3+}$-doped $GeO_2-SiO_2$ thin films by a sol-gel thin coating process and studied them for photonic applications. Rajni and coworkers (Rajni, et al. *Journal of The Electrochemical Society.* 2005, 152, G456-G459) fabricated an inorganic $20GeO_2:80SiO_2$ thin film also by a sol-gel thin coating process, choosing this ratio due to its lack of clustering in the films.

Monoliths are continuous beds of porous material and can be chemically bonded to the inner walls of a capillary (Hayes & Malik, *Anal. Chem.* 2000, 72, 4090-4099). Compared to organic, continuous polymeric monoliths, silica-based monoliths prepared by the sol-gel techniques are mechanically stronger and have superior durability in the presence of solvents (Wu, et al. *J. Chromatgr. A*. 2008, 1184, 369-392). The advantages of monoliths include the ability to control its morphology and the fritless design when used as a column. The size of through-pores, mesopores and skeleton can be controlled by the amount or type of monomer used and by the ratio of monomer, porogen and catalyst (Kato, et al., *J. Chromatgr. A*. 2002, 961, 45-51).

Monoliths can be chemically modified after fabrication to obtain the desired stationary phase, which can be accomplished in a monomeric or polymeric procedure. A monomeric procedure can be carried out through a direct reaction between silica and the reagent with the desired functional moiety. It can also be accomplished through the introduction of a spacer followed by the reaction of the ligand that introduces the desired functional group. In the case of a polymeric procedure, either a spacer or an anchor is bonded to the silica before the chemical modification is performed (Núñez, et al. *J. Chromatogr. A*. 2008, 1191, 231-2).

These modifications allow for the development of monolithic columns suitable for different separation modes in HPLC, including ion-exchange, reversed phase (RP), hydrophilic interaction chromatography (HILIC), chiral separations and mixed modes (Núñez, et al. *J. Chromatogr. A*. 2008, 1191, 231-2). Dulay et al. (Dulay, et al., *J. Sep. Sci*. 2002, 25, 3) chemically modified sol-gel monoliths by silanizing the sol-gel surface with organochlorosilane or organoalkoxysilane coupling reagents. In 2004, a coating procedure for the modification of a silica monolith by forming a monolithic column with zirconia surface was introduced. Compared to conventional silica monoliths, the zirconia surface increased the stability of the monolith and even facilitated the separation of basic compounds (Shi, et al. *Talanta*. 2004, 63, 593). Shi et al. (Shi, et al. *J. Non-Cryst. Solids*. 2006, 352, 4003-4007) developed a novel urea-formaldehyde template for the synthesis of porous inorganic oxide monoliths where silica, zirconia and titania monoliths were successfully prepared. The hydrophilic nature of the template made it possible for the elimination of organic precursors for the preparation of these monoliths (Shi, et al. *J. Non-Cryst. Solids*. 2006, 352, 4003-4007). Svec et al. have contributed to the fabrication of microchannel monolithic stationary phases in microfluidic devices for chromatographic separation and sample SPE (Yu, et al. *Electrophoresis*. 2000, 21, 120; Rohr, et al. *Electrophoresis*. 2001, 22, 3959; Yu, et al. *Anal. Chem*. 2001, 73, 5088; Yu, et al. *J. Polym. Sci. Part A-Polym. Chem*. 2002, 40, 755).

While monolithic columns are simple to fabricate and have been successfully employed in capillary electrochromatography (CEC) and high-performance liquid chromatography (HPLC), the existing technology suffers from several limitations. For instances, monolithic columns often crack, shrink, have structural imperfections (e.g., presence of granular voids near the capillary walls), cannot withstand high pressures, and are difficult to seal. Drying produces a pressure gradient in the liquid phase of a gel, leading to a differential shrinkage of the network (Brinker & Scherer, *Sol-Gel Science: The Physics and Chemistry of Sol-Gel Processing*, Academic Press: San Diego, Calif., 1990, pp 444-99). Cracking is often attributed to a pore size distribution on a gel. When larger pores are emptied upon evaporation of solvent, the wall adjoining pores is subjected to an uneven stress that can cause cracking (Brinker & Scherer, *Sol-Gel Science: The Physics and Chemistry of Sol-Gel Processing*, Academic Press: San Diego, Calif., 1990, pp 444-99). Accordingly, improved chromatographic and extraction columns are needed.

BRIEF SUMMARY

The present invention provides germania-silica-based sol-gel monoliths that form the solid-phase material for extraction, isolation, preconcentration, and separation of analytes. In one embodiment, the germania-silica-based sol-gel monolith can be used to coat surfaces of the inner walls of extraction and chromatographic columns. In a preferred embodiment, the germania-silica-based sol-gel monoliths can be used as solid-phase material in capillary microextraction (CME). Also provided are methods of preparing the germania-silica-based sol-gel monolith of the present invention.

In one embodiment, the present invention provides sol-gel germania-silica monolith formed from sol-gel precursors comprising a germanium alkoxide and/or hydrolyzed germanium alkoxide, an alkoxysilane and/or hydrolyzed alkoxysilane, and a polyglycol.

In a specific embodiment, the present invention provides sol-gel germania/silica/PEG-based hybrid organic-inorganic monolithic materials for use in capillary microextraction (CME). In one embodiment, sol-gel reactions were carried out within fused silica capillaries (0.32 mm I.D.) to fabricate monolithic capillaries. This monolith was very porous and able to withstand liquid-phase operations involving elevated pressures. Detection limits in the nanogram/liter range were accomplished with CME sol-gel germania PEG monolithic capillaries on-line coupled to high-performance liquid chromatography (HPLC) with UV detection. Advantageously, the sol-gel hybrid silica/germania/PEG monoliths of the invention demonstrated stability under acidic and basic conditions, and survived 18 hours of exposure to 1.0 M HCl (pH≈0.0) and 0.1 M NaOH (pH≈13.0).

In another embodiment, the present invention provides a method of preparing solid-phase material comprising the sol-gel germania-silica monolith for extraction of trace analytes. In one embodiment, the method comprises: preparing a sol solution by mixing reagents comprising a germanium alkoxide and/or hydrolyzed germanium alkoxide, an alkoxysilane and/or hydrolyzed alkoxysilane, and a polyglycol, and whereby the sol solution forms into sol-gel germania-silica monolith via polycondensation. In one embodiment, the method further comprises mixing the reagents with a catalyst, exemplified herein by trifluoracetic acid.

Also provided is a method for extracting, preconcentrating, and/or isolating trace analytes in a sample, comprising: contacting a sample containing one or more analytes with the solid-phase microextraction material of the invention; and desorbing the analytes from the sol-gel germania-silica monolith.

BRIEF DESCRIPTION OF THE DRAWINGS

For a fuller understanding of the invention, reference should be made to the following detailed description, taken in connection with the accompanying drawings, in which.

DETAILED DESCRIPTION

Figure 1:
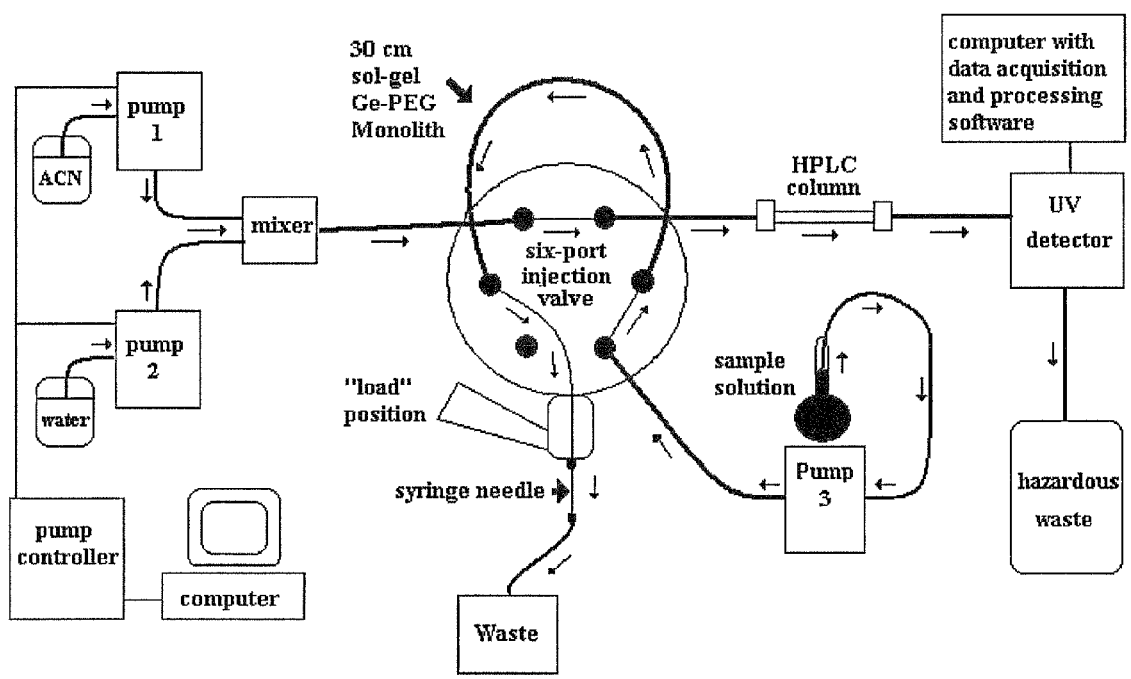
FIG. 1 illustrates the experimental setup used to carry out CME-HPLC experiments using the sol-gel germania-silica PEG monolith. To perform extraction, the sol-gel monolith is installed as an external sampling loop on a six-port HPLC injection valve. An HPLC pump (pump 3) was connected to the waste line on the injection valve, and a syringe needle, connected to a piece of PEEK tubing, was inserted into the needle port on the injection valve. Aqueous samples containing analytes were pumped (1 mL/min flow rate) into the HPLC injection valve via the waste line, through the sol-gel monolith, and finally out through the needle port into an appropriate waste container. To perform analysis, pump 3 was turned off, then the HPLC injection valve was switched to the inject position. This allowed the mobile phase to flow through the sol-gel germania-silica monolith, which desorbed the analytes and transferred them into the HPLC column for separation, followed by subsequent UV detection.

The present invention provides germania-silica-based sol-gel monoliths that form the solid-phase material for extraction, isolation, preconcentration, and separation of analytes. In one embodiment, the germania-silica-based sol-gel monolith can be used to coat surfaces of the inner walls of extraction and chromatographic columns. Also provided are methods of preparing the germania-silica-based sol-gel monolith of the present invention.

In one embodiment, the present invention provides monolithic columns surface-coated with germania-silica-based hybrid material for extraction, isolation, preconcentration, and separation of the target analyte(s). Germania is an isostructural analog to silica. Thus, mixed germania-silca-based hybrid sorbents and stationary phases are expected to closely resemble their silica-based counterparts. Surprisingly, the present inventors discovered that mixed germania-silica-based organic-inorganic hybrid monolithic beds (containing even a small percentage of germania) possess significantly superior pH stability, when compared to the stability of silica-based monoliths that do not contain germanium. This discovery is counter-intuitive.

In one embodiment, the present invention provides silica-germania based sol-gel monolithic columns, suitable for use in capillary microextraction (CME) in hyphenation with high-performance liquid chromatography (HPLC). In one embodiment, the monolithic bed was created within a fused silica capillary using a properly designed sol solution comprising a silica precursor, a germania precursor, a sol-gel active organic polymer, a catalyst, and an appropriate solvent system. The capillary was filled with the sol solution which, due to sol-gel reactions, gradually turned into a porous monolithic bed covalently anchored to the surface of the capillary. The monolithic capillary provided several tens of folds higher extraction efficiency compared with open tubular extraction columns with identical coating composition.

Advantageously, the sol-gel germania-silica PEG monolith can be used for the preconeentration and extraction of analytes ranging from polar to non-polar. The PEG group contains polar hydroxyl groups and non-polar hydrocarbon chains. The polar hydroxyl groups allow for the extraction of polar analytes with excellent detection limits and non-polar hydrocarbon chains allow for the extraction of both moderately polar and non-polar analytes with low detection limits. In comparison to previously fabricated sol-gel octyl monoliths, the sol-gel germania-silica PEG monlith was 743 to 1000 times more sensitive in the extraction of PAHs. Additionally, the monolith of the present invention can withstand high pressures, organic solvents, acidic (pH≈0.0) and basic (pH≈13.0) conditions and does not crack or shrink as most monoliths tend to.

One aspect of the invention provides sol-gel germania-silica monolithic solid-phase material for extraction of trace analytes. In one embodiment, a surface of the solid-phase material comprises sol-gel germania-silica monolith, wherein the sot-gel germania-silica monolith is formed from sol-gel precursors comprising a germania-based precursor, a silica-based precursor, and a sol-gel active polymer. In one embodiment, sol-gel germania-silica monolith is formed from sol-gel precursors comprising a germanium alkoxide and/or hydrolyzed germanium alkoxide, an alkoxysilane and/or hydrolyzed alkoxysilane, and a polyglycol.

Germanium alkoxides useful according to the present invention include, but are not limited to, mon-, di-, tri-, and tetraalkoxy germanane, such as, tetraethoxygermane, tetramethoxygermane, tetrapropoxygermane, and tetrabutoxygermane. The germania-based sol-gel precursor can also be hydrolyzed germanium alkoxide monomers, dimers, and/or trimers.

Alkoxysilanes useful according to the present invention include, but are not limited to, mon-, di-, tri-, and tetraalkoxy, such as, tetramethoxysilane, trimethoxysilane, triethoxysilane, methyltrimethoxysilane, ethyltrimethoxysilane, n-propyltrimethoxysilane, dimethyldimethoxysilane, diisopropyldimethoxysilane, diisobutyl dimethoxysilane, isobutyltrimethoxysilane, n-hexyltrimethoxysilane, and n-octyltrimethoxysilane. The silica-based sol-gel precursor can also be hydrolyzed alkoxysilane monomers, dimers, and/or trimers.

In one embodiment, the sol-gel active polymer is hydroxyl-terminated. In one embodiment, the sol-gel active polymer is a polyglycol. Polyglycols useful according to the present invention include, but are not limited to, polyethylene glycol, methoxypolyethylene glycol, polypropylene glycol, and polybutylene glycol. In an embodiment, the sol-gel active polymer is polypropylene glycol. In certain embodiments, the sol-gel active polymer is selected from poly(dimethylsiloxane), 3-amino-propyltrimethoxysilane, 3-cyanopropyltriethoxysilane, poly(dimethyldiphenylsiloxane), or a combination thereof. In another embodiment, the sol-gel active polymer is a co-polymer.

In certain embodiments, the sol-gel germania-silica monolith of the present invention is formed from hydrolysis and polycondensation of precursors comprising tetraethoxygermane, tetramethoxysilane, and polyethylene glycol.

In one embodiment of the sol-gel germania-silica monolith of the invention, the molar ratio of germanium/silicon is lower than about 1:10, 1:9, 1:8, 1:7, 1:6, 1:5, 1:4, 1:3, 1:2, 1:1, 2:1, 3:1, 4:1, 5:1, 6:1, 7:1, or 8:1. In certain embodiments of the sol-gel germania-silica monolith of the invention, the molar ratio of germanium/silicon is higher than about 1:9, 1:8, 1:7, 1:6, 1:5, 1: 4, 1:3, 1:2, 1:1, 2:1, 3:1, 4:1, 5:1, 6:1, 7:1, 8:1, or 9:1.

In one embodiment, the sol-gel germania-silica monolith forms the solid-phase material for microextraction of analytes. In another embodiment, the present invention provides a solid-phase material for extraction, wherein a surface of the solid-phase material is coated with the sol-gel germania-silica monolith. In one embodiment, the sol-gel germania-silica monolith is chemically bonded (such as via covalent bonds) to a surface of the solid-phase material. In one embodiment, the solid-phase material comprises fused silica, wherein the sol-gel germania-silica monolith is chemically bonded to the fused silica.

In one embodiment, the present invention provides a microextraction capillary, wherein a surface of the inner walls of the capillary is coated with the sol-gel germania-silica monolith. In certain embodiments, the present invention provides chromatographic and/or extraction columns, such as columns for use in gas chromatography and liquid chromatography, where the surfaces of the inner walls of the columns are coated with the sol-gel germania-silica monolith of the invention.

Another aspect of the invention provides a method of preparing solid-phase material comprising the sol-gel germania-silica monolith of the invention for extraction of trace analytes. In one embodiment, the method comprises: preparing a sol solution by mixing reagents comprising a germanium alkoxide and/or hydrolyzed germanium alkoxide, an alkoxysilane and/or hydrolyzed alkoxysilane, and a polyglycol and/or hydrolyzed polyglycol, and whereby the sol solution forms into sol-gel germania-silica monolith via polycondensation. In one embodiment, the method further comprises mixing the reagents with a catalyst, exemplified herein by trifluoracetic acid.

In one embodiment, the sol solution is prepared by mixing the reagents in the following order: a polyglycol, a germanium alkoxide and/or hydrolyzed germanium alkoxide, trifluoracetic acid, and an alkoxysilane and/or hydrolyzed alkoxysilane. In a preferred embodiment, the sol-gel reagents comprise tetraethoxygermane, tetramethoxysilane, and polyethylene glycol. In one embodiment, the reagents further comprise water.

In one embodiment, the present invention provides a method for preparing a microextraction capillary, wherein the method comprises:

a) filling the capillary with the sol solution, wherein the sol solution is prepared by mixing reagents comprising a germanium alkoxide and/or hydrolyzed germanium alkoxide, an alkoxysilane and/or hydrolyzed alkoxysilane, and a polyglycol and/or hydrolyzed polyglycol, and whereby the sol solution forms into sol-gel germania-silica monolith bounded to a surface of the inner walls of the capillary; and b) purging the capillary of unbound sol solution.

In one embodiment, the method for preparing the microextraction capillary further comprises: thermal conditioning the capillary after step (b). In certain embodiments, the thermal conditioning of the coated capillary is performed using temperature-programmed heating, wherein the heat increases from about 40° C. to about 280° C., at an increment of about 1° C./minute, followed by a holding at about 280° C. for two hours. In certain alternative embodiments, the beginning temperature of the thermal conditioning step is about 40° C. to about 60° C., or at any temperature therebetween. In certain alternative embodiments, the final temperature of the thermal conditioning step is about 240° C. to about 320° C., or at any temperature therebetween. In certain alternative embodiments, the heat increases at a rate from about 1° C./minute to about 5° C./minute, or at any rate therebetween. In certain alternative embodiments, the final temperature is held for about 1, 1.5, 2, 2.5, 3, 3.5, 4, or 5 hours. The thermal conditioning of the coated column can be performed more than once.

In one embodiment, the inner walls of the capillary column are incubated with the sol solution for about 10, 15, 20, 25, 30, 35, 40, 45, 50, 55, or 60 minutes. In one embodiment, the sol solution chemically binds to the inner walls of the capillary column to form sol-gel germania-based coated capillary column.

A further aspect of the invention provides a method for extracting, preconcentrating, and/or isolating trace analytes in a sample, comprising:

contacting a sample containing one or more analytes with the solid-phase microextraction material of the invention; and desorbing the analytes from the sol-gel germania-silica monolith.

In one embodiment, the sol-gel germania-silica monolith of the invention are used as solid-phase material for capillary microextraction, gas chromatography (GC), capillary electrophoresis, capillary electrochromatography, inductively coupled plasma mass spectrometry, and/or high-performance liquid chromatography (HPLC).

Advantageously, the monolith of the present invention has excellent pH stability, and can be used under pH conditions across the ranges of 0 to 14, 0 to 13, 0 to 12, 1 to 14, I to 13, 1 to 12, or at any pH therebetween. Further, the monolith of the present invention can be used for extraction, preconcentration, analysis and/or isolation of analytes from a wide range of chemical classes including, but not limited to, polycyclic aromatic hydrocarbons (PAH), ketones, alcohols, phenols, amines, or combinations thereof. In a preferred embodiment, the monolith of the present invention can be used for extraction, preconcentration, analysis, and/or isolation of one or more analytes selected from Table 2.

MATERIALS AND METHODS

Equipment

A Micro-Tech Scientific (Vista, Calif., USA) Ultra Plus HPLC system equipped with a Linear UVIS 200 variable wavelength UV detector was utilized to carry out on-line coupled CME-HPLC experiments using the sol-gel germania-silica PEG monoliths. A Hitachi L6000 HPLC pump was used to pump the aqueous samples through the sol-gel germania monolith for extraction. The HPLC separations were performed using a reversed-phase Luna $C_{18}$ column (15 cm×4.6 mm I.D.). Nanopure deionized water (15 M$\Omega$) was generated on a Barnstead model 04741 Nanopure deionized water system (Barnstead/Thermodyne, Dubuque, Iowa, USA). For on-line data collection and processing, Chrom Perfect version 3.5 computer software (Justice Laboratory Software, Denville, N.J., USA) was employed.

Chemicals and Materials

Fused-silica capillary (0.32 mm i.d.) was purchased from Polymicro Technologies, Inc. (Phoenix, Ariz.). Polypropylene centrifuge tubes, HPLC grade methylene chloride, methanol and acetonitrile (ACN) were purchased from Fisher Scientific (Pittsburgh, Pa.). Polycyclic aromatic hydrocarbons (naphthalene, acenaphthene, and fluorene), ketones (benzophenone, coumarin, and trans-chalcone), amines (o- and m-toluidine, and N-methylaniline), and phenols (2,3-dichlorophenol, 2-chlorophenol, 3,4-dimethylphenol, 3,5-dimethylphenol) were purchased from Aldrich (Milwaukee, Wis., USA). Tetramethoxysilane (TMOS), 99%, and trifluoroacetic acid (TFA), 99% were purchased from Acros (New Jersey, USA). Anthracene and 4'phenylacetophenone were purchased from Eastman Kodak (Rochester, N.Y., USA). Diphenylamine was purchased from J. T. Baker (Phillipsburg, N.J., USA). Aldehydes (p-nitrobenzaldehyde and m-tolualdehyde) were purchased from Acros (Milwaukee, Wis., USA). 1-naphthylamine and 2-naphthol were purchased from Matheson, Coleman, and & Bell (Norwood, Ohio, USA). Benzhydrol was purchased from Sigma (St. Louis, Mo.). Resorcinol was purchased from Spectrum (Gardena, Calif.). Poly(ethylene glycol) (PEG) (MW-600) was purchased from Sigma Aldrich (Allentown, Pa.). Tetraethoxygermane (TEOG) was purchased from Gelest, Inc. (Morrisville, Pa.). Rocksett, an engineering adhesive was purchased from Flexbar Corp. (Long Island, N.Y.).

Following are examples that illustrate procedures for practicing the invention. These examples should not be construed as limiting.

EXAMPLES 1

Preparation of Capillary Coated with Sol-Gel Germania-Silica PEG Monoliths

Pretreatment of Fused-Silica Capillary Inner Surface

A 321 μm i.d. capillary (50 cm) was sequentially rinsed with 4 mL each of methylene chloride, methanol and 15 M$\Omega$·cm water at 20 psi (138 kPa). The ends of the capillary were then sealed with an oxyacetelene torch so that a thin layer of water remained on the inner surface of the capillary. This was followed by thermal treatment of the capillary at 300° C. for two hours in a gas chromatography (GC) oven. The ends of the capillary were then cut open using an alumina wafer followed by further thermal conditioning and simultaneous purging with helium gas. Temperature programming began at an initial temperature of 40° C., increasing at a rate of 5° C./min, and reaching a final temperature of 300° C. which was held constant for two hours. After this, the capillary was ready for the creation of a monolithic bed using a sol solution.

Preparation of the Sol-Gel Solution

The sol solution was prepared by sequentially adding the following ingredients to a thoroughly cleaned microcentrifuge tube: 0.1348 g PEG (MW=600), 30 μL TEOG, 200 μL TFA containing 1% $H_2O$, 200 μL TFA containing 5% $H_2O$, and 200 μL TMOS. The chemical structures of these reagents are shown in Table 1. After each addition to the centrifuge vial, the solution was vortexed for 10 seconds. After all the reagents were added, the solution was centrifuged for four minutes at 14000 rpm. The supernatant was then transferred from the centrifuge tube to a clean vial for further use in the preparation of a monolithic bed in a fused silica capillary.

TABLE 1

Illustration of Names and Structures of Sol-Gel Reagents
Used to Fabricate Monolithic Columns

| Reagent Function and Name | Structure |
|---|---|
| Sol-gel coprecursor-<br>Tetraethoxygermane (TEOG) | $C_2H_5O-Ge(OC_2H_5)_3$ |
| Sol-gel co-precursor-<br>Tetramethoxysilane (TMOS) | $H_3CO-Si(OCH_3)_3$ |
| Catalyst-Trifluoracetic acid (TFA) | $F_3C-C(=O)-OH$ |
| Carbowax-PEG polymer | $HO-(CH_2CH_2O)_n-H$ |

Preparation of Sol-Gel Monolithic Capillaries

Prior to filling the capillary with the sol solution, one of its ends was sealed with an oxyacetylene torch. The capillary was filled with the sol solution at 50 psi using a gas pressure operated filling/purging device (Hayes & Malik, *J. Chromatogr. B.* 1997, 695, 3-13) and left overnight undisturbed. The capillary was then removed from the device and the open end of the capillary was sealed with the engineering adhesive Rocksett by dipping it in the sealant, forming a bulb at the end. The capillary was wrapped on a basket and treated in a GC oven according to the following temperature program: from 40° C. to 280° C. at a rate of 1° C./min and holding at the final temperature for two hours.

Figure 2:
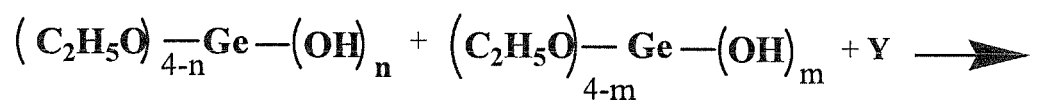
FIG. 2 illustrates one embodiment of one step of the sol-gel reaction scheme of the present invention.
Figure 2:
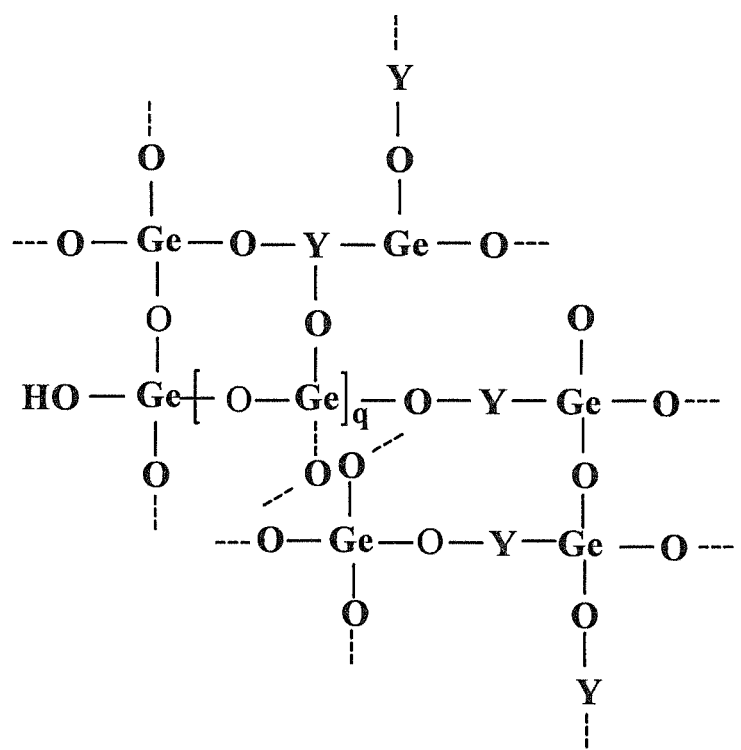
Figure 3:
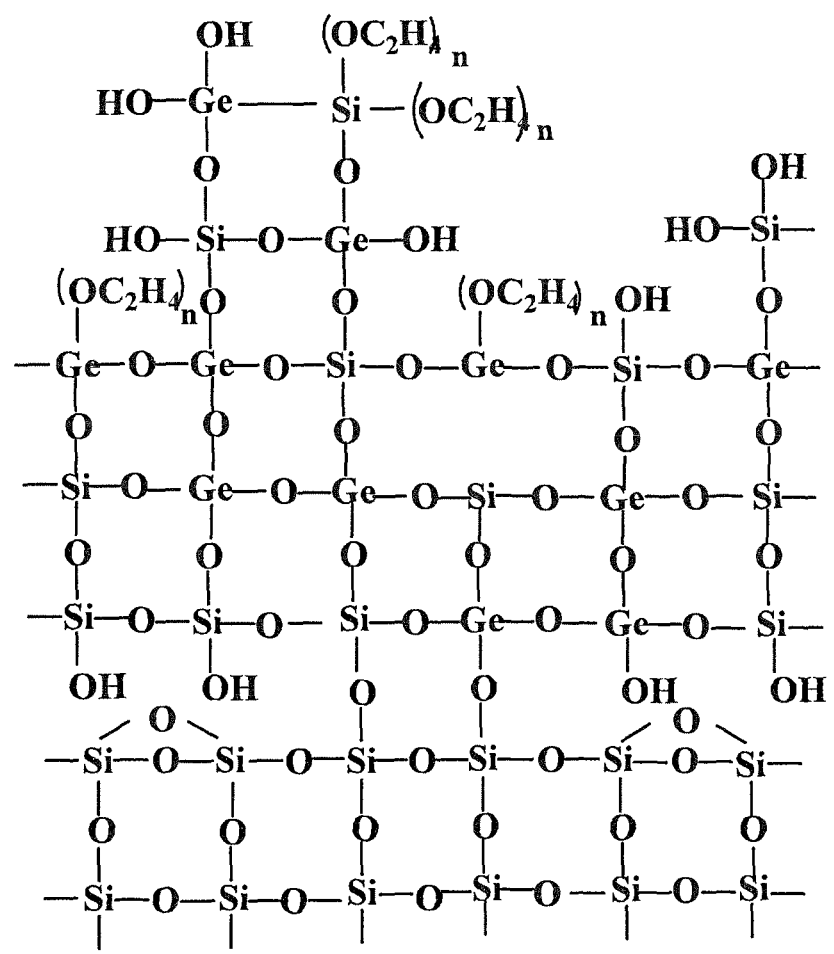
FIG. 3 illustrates the chemical structure of one embodiment of the sol-gel germania-silica PEG monolith.

In the course of formation of the sol-gel monolith, the gelation of the sol forms a network in a continuous liquid phase. The precursors are usually metal alkoxides, which react readily with water and the alkoxysilanes such as TMOS. Sol-gel reactions proceed via hydrolysis followed by polycondensation where a three dimensional sol-gel network is formed, seen in FIGS. 2 and 3. Polycondensation can occur with the linkage of additional silanol groups to form a silicate network (Legido-Quigley, et al. *Electrophoresis.* 2003, 24, 917-944). The sol solution is clear immediately after preparation and introduction into the capillary. Approximately 5-10 minutes after gelation, the sol-gel slowly turns iridescent as the monolith forms. It is apparent once the fused silica capillary is filled with the monolithic bed as it appears to be white in nature.

Figure 4A:
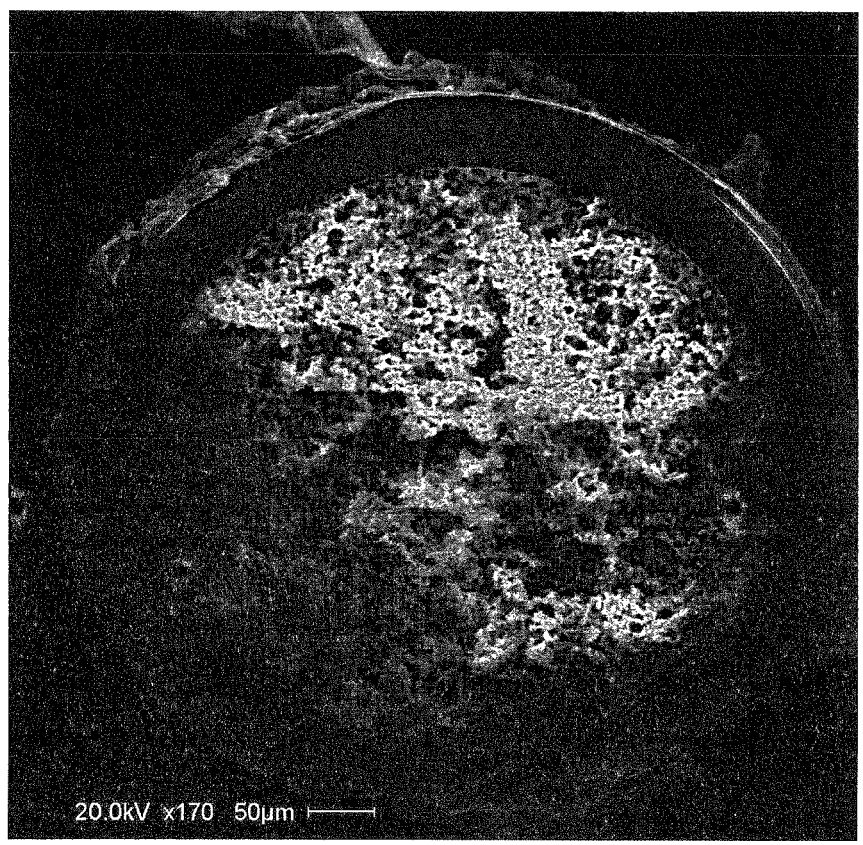
FIGS. 4A and 4B are scanning electron micrographs of the the sol-gel germania-silica PEG monolith. A magnification at 150×; B magnification at 1500×.
Figure 4B:
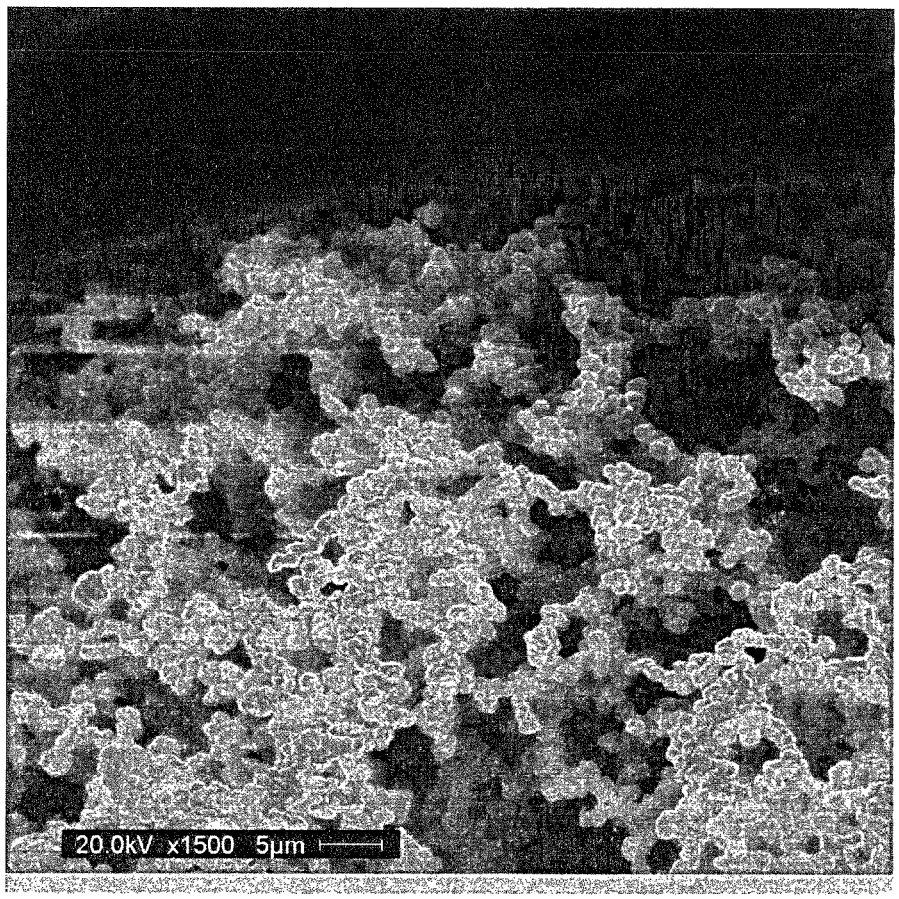

Sol-gel monoliths exhibit a high surface area due to their mesoporosity and also have a low pressure drop over the bed due to the presence of macropores (Yang, et al. *New J. Chem.* 2004, 28, 1520-1525). To demonstrate that the sol-gel germania/silica/PEG organic/inorganic hybrid monolith had formed within the fused silica capillary, scanning electron microscopy (SEM) images were obtained, as shown in FIGS. 4A and B. The SEM in FIG. 4A indicates that a continuous sol-gel monolith has formed, with no gaps, within the fused silica capillary. A SEM with higher magnification was also obtained to study the morphology of the germania-PEG monoliths, as shown in FIG. 4B. The SEMs reveal an interconnected porous network of spherical structures and mesopores. These mesopores allow for mass transfer of analytes from the mobile phase to the chromatographic active sites for separation (Dulay, et al. *Anal. Chem.* 2001, 73, 3921-3926).

EXAMPLE 2

Capillary Microextraction and On-Line HPLC Analysis (CME-HPLC) Using Sol-Gel Germania-Silica PEG Monoliths The experimental setup used to perform capillary microextraction on a sol-gel germania-silica PEG monolithic bed on-line coupled to an HPLC system is shown in FIG. 1.

To perform capillary microextraction, both ends of a 30 cm segment of the sol-gel germania-silica PEG monolithic capillary (0.32 mm I.D.) were fitted with polyether ether ketone (PEEK) tubing sleeves (0.508 mm×1.575 mm) and appropriate nuts and ferrules. Next, this segment was installed as an external sampling loop on a six-port HPLC injection valve. A separate HPLC pump (pump 3, FIG. 1) was connected to to the waste line of the injection valve. In the HPLC injection valve, a typical external sampling loop is loaded by inserting a syringe into the needle port and pushing down on the plunger, causing the sample solution to fill the external sampling loop, and then drip out of a waste line connected to the appropriate port on the injection valve. In contrast, in the case of on-line CME-HPLC using a sol-gel germania-silica PEG monolith as an external sampling loop, this flow is reversed and a syringe needle connected to a segment of PEEK tubing was inserted into the needle port of the injection valve, which was in the "load" position. Extraction was performed by pumping a sample solution through the sol-gel germania-silica PEG monolith at a flow rate of 1 mL/min, allowing enough time (30-50 min, depending on the analyte type) for extraction equilibrium to be established between the sample solution and the sol-gel germania-silica PEG monolith. After this, pump 3 was stopped, and the injection valve was switched to the "inject" position. This allowed the HPLC mobile phase to flow through the sol-gel germania-silica PEG monolith and to desorb the extracted analytes and transfer them into the HPLC column for separation. Both isocratic and gradient elution with ACN/water mobile phases were utilized in order to achieve appropriate separation of the extracted analytes. Between two consecutive analyses, the sol-gel germania-silica PEG monolith was rinsed with approximately 10 mL of methanol using pump 3.

To determine the time required for establishing extraction equilibrium between the sol-gel germania-silica PEG monolith and analytes, extraction profiles were investigated for five different compounds, each representative of a different chemical class. This was accomplished by conducting three replicate extractions for each of these analytes for each of the following extraction periods: 10 min, 20 min, 30 min, 40 min, 50 mm, and 60 mm. Next, the average HPLC peak areas for each extraction period were plotted against their respective extraction times. The time required for establishing extraction equilibrium between the sol-gel germania-silica PEG monolith and the analytes was determined by the point on the x-axis beyond which the peak area ceases to increase with respect to extraction time.

Figure 5:
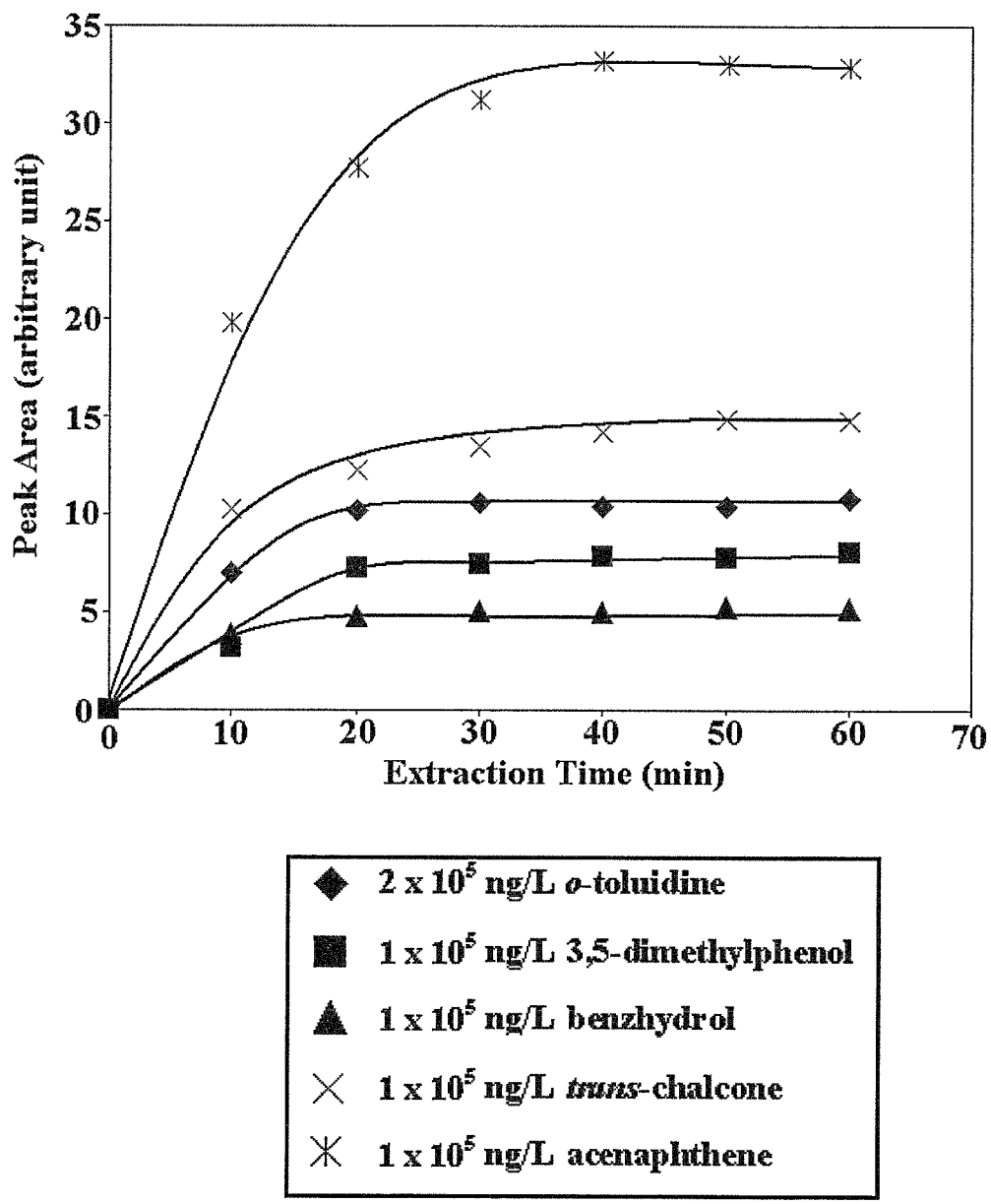
FIG. 5 shows extraction profiles for o-toluidine, 3,5-dimethylphenol, benzhydrol, trans-chalcone, and acenaphthene, using the sol-gel germania-silica PEG monolith of the present invention.

FIG. 5 shows the extraction profiles. For amines, equilibrium was established within approximately 20 min of extraction. Phenols required between 20 and 30 min to reach extraction equilibrium. To attain extraction equilibrium, alcohols, PAHs, and ketones required 30, 40, and 50 min, respectively. This equilibrium data was further utilized in subsequent experiments involving extraction of analytes from diverse chemical classes.

The sol-gel mixed germania-silica PEG monolith can efficiently extract polar analytes with excellent detection limits (0.5 ng/L to 264.0 ng/L). This is because the monolith of the present invention contained PEG, a polar polymer, as the organic component. Among the polar analytes extracted on the monolith were phenols, alcohols, and amines. The HPLC peak area RSD values and detection limit data for all analytes are presented in Table 2.

TABLE 2

HPLC peak area repeatability and detection limit data for phenols, alcohols, amines, aldehydes, ketones, and PAHs in CME-HPLC using a sol-gel germania-silica PEG monolith.

| Chemical Class | Chemical Name | Peak Area RSD (n = 3) (%) | Detection Limits (S/N = 3) (ng/L) |
| --- | --- | --- | --- |
| Phenols | 2,3-dichlorophenol | 1.9 | 26.9 |
| | 2-chlorophenol | 4.6 | 85.4 |
| | 3,4-dimethylphenol | 5.6 | 44.1 |
| | 3,5-dimethylphenol | 6.7 | 33.2 |
| Alcohols | benzhydrol | 9.2 | 7.5 |
| | resorcinol | 4.0 | 264.0 |
| | 2-naphthol | 2.9 | 71.5 |
| Amines | diphenylamine | 4.5 | 5.7 |
| | o-toluidine | 4.0 | 9.9 |
| | m-toluidine | 6.1 | 10.4 |
| | N-methylaniline | 3.4 | 0.5 |
| | 1-naphthylamine | 9.7 | 9.6 |
| Aldehydes | nitrobenzaldehyde | 8.7 | 24.1 |
| | m-tolualdehyde | 2.4 | 1.1 |
| Ketones | 4'phenylacetophenone | 2.7 | 0.5 |
| | benzophenone | 5.2 | 1.9 |
| | coumarin | 1.6 | 0.4 |
| | trans-chalcone | 8.5 | 2.2 |
| PAHs | anthracene | 2.7 | 3.1 |
| | fluoranthene | 7.6 | 8.1 |
| | naphthalene | 6.7 | 64.4 |
| | acenaphthene | 6.2 | 13.2 |
| | fluorene | 8.8 | 10.9 |

Extraction conditions: 30 cm x 0.32 mm I.D. sol-gel germania-silica PEG monolith, 40 min extraction at room temperature. HPLC conditions: 15 cm x 4.6 mm I.D. Luna $C_{18}$ column, isocratic elution with $ACN/H_2O$ (50/50 for phenols and alcohols, 60/40 for amines, aldehydes, and ketones, 65/35 for PAHs) mobile phases, 1 ml/min flow rate, UV detection at 200 nm for phenols, alcohols, amines, aldehydes, and ketones, 254 nm for PAHs, ambient temperature for all.

Figure 6:
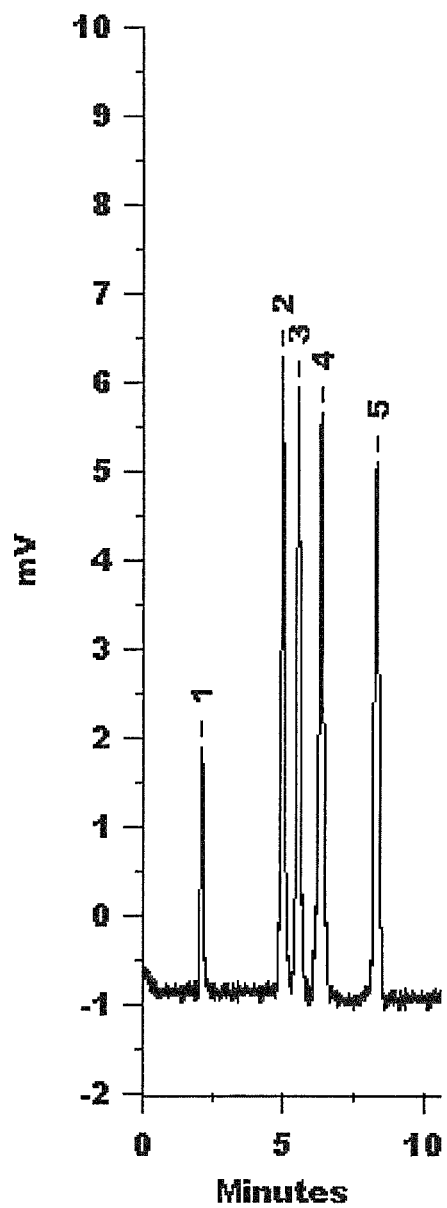
FIG. 6 shows CME-HPLC-UV analysis of phenols and alcohols, using the sol-gel germania-silica PEG monolith of the present invention. Extraction conditions are: 30 cm×0.32 mm I.D. monolith, 30 min extraction at room temperature (1 mL/min flow rate). HPLC conditions are: 15 cm×4.6 mm I.D. Luna $C_{18}$ column, isocratic elution 50/50 ACN/$H_2O$, 1 ml/min flow rate, UV detection at 200 nm, ambient temperature. 1=Resorcinol ($1\times10^5$ ng/L), 2=2-chlorophenol ($1\times10^5$ ng/L), 3=3,4-dimethylphenol ($5\times10^4$ ng/L), 4=2-naphthol ($1\times10^5$ ng/L), 5=benzhydrol ($1\times10^4$ ng/L).

For phenols and alcohols, the observed detection limits ranged from 26.9 to 85.4 ng/L and from 7.5 to 264.0 ng/L, respectively. The sol-gel mixed germania-silica PEG monolith also demonstrated good HPLC peak area RSD values (1.9 to 9.2%) for phenols and alcohols. A chromatogram depicting on-line CME-HPLC analysis of phenols and alcohols is shown in FIG. 6.

The differences in the detection limits observed for the phenols and alcohols can be attributed to differences in UV absorption characteristics of the analytes and different affinities of the analytes for the sol-gel germania-silica PEG monolith.

Figure 7:
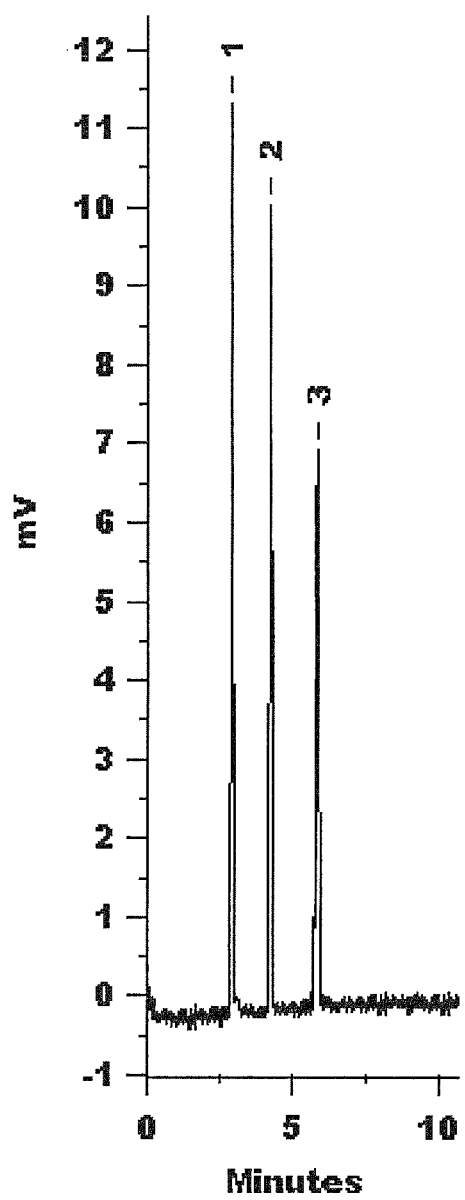
FIG. 7 shows CME-HPLC-UV analysis of amines, using the sol-gel germania-silica PEG monolith of the present invention. Extraction conditions are: 30 cm×0.32 mm I.D. monolith, 30 min extraction at room temperature (1 mL/min flow rate). HPLC conditions are: 15 cm×4.6 mm I.D. Luna $C_{18}$ column, gradient elution 65/35 to 80/20 ACN/H20 in 10 min, 1 ml/min flow rate, UV detection at 200 nm, ambient temperature. 1 =o-toluidine ($1\times10^4$ ng/L), 2=N-methylaniline ($5\times10^2$ ng/L), 3=diphenylamine ($5\times10^3$ ng/L).

The mixed sol-gel germania-silica PEG monolith can extract aromatic amines with detection limits between 0.5 and 10.4 ng/L and HPLC peak area RSD values ranging from 3.4 to 9.7%. A chromatogram illustrating the separation of three aromatic amines is presented in FIG. 7.

Figure 8:
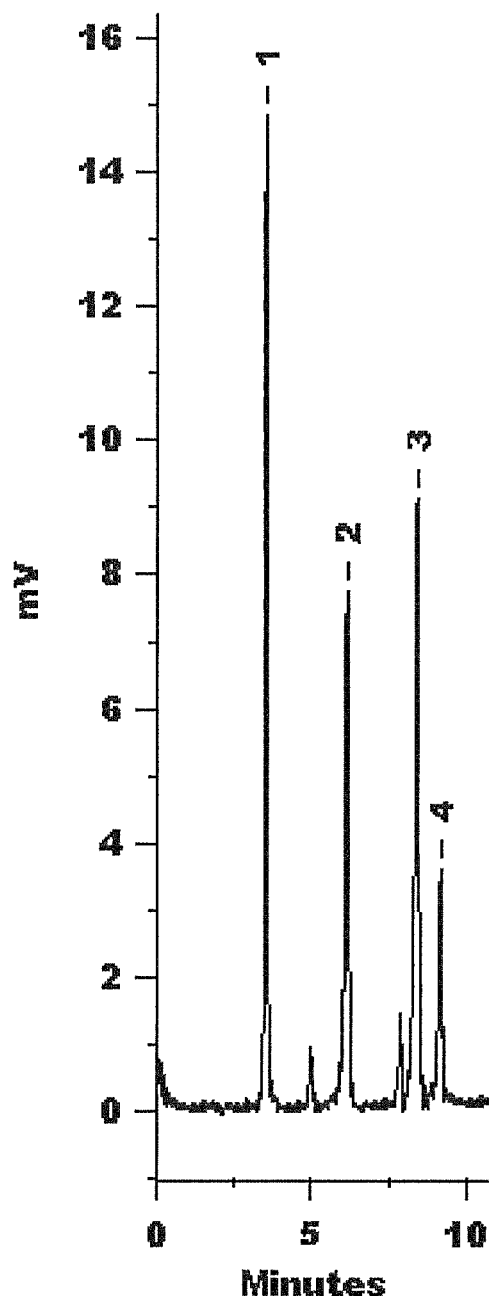
FIG. 8 shows CME-HPLC-UV analysis of aldehydes and ketones, using the sol-gel germania-silica PEG monolith of the present invention. Extraction conditions are: 30 cm×0.32 mm I.D. monolith, 50 min extraction at room temperature (1 mL/min flow rate). HPLC conditions are: 15 cm×4.6 mm I.D. Luna $C_{18}$ column, gradient elution (55/45 to 75/25 ACN/$H_2O$ over 10 min), 1 ml/min flow rate, UV detection at 200 nm, ambient temperature. 1=coumarin ($4\times10^2$ ng/L), 2=m-tolualdehyde ($8\times10^2$ ng/L), 3=4'phenylacetophenone ($4\times10^2$ ng/L), 4=trans-chalcone ($8\times10^2$ ng/L).

The sol-gel mixed germania-silica PEG monolith was also tested for its ability to extract moderately polar analytes, such as ketones and aldehydes. Four ketones and two aldehydes were successfully extracted using the monolith of the invention. For ketones, the detection limits ranged from 0.4 ng/L to 2.2 ng/L. For the two aldehydes extracted, p-nitrobenzaldehyde and m-tolualdehyde, the detection limits were 24.1 ng/L and 1.1 ng/L, respectively. For these aldehydes and ketones, the HPLC peak area RSD values ranged from 1.6% to 8.7%. Since PEG contains nonpolar carbon chains, as well as polar hydroxyl groups, it is capable of extracting moderately polar compounds, such as aldehydes and ketones. The HPLC peak area RSD values and detection limit data for aldehydes and ketones is presented in Table 2. A chromatogram depicting the separation of analytes in a sample containing an aldehyde and three ketones extracted using the sol-gel germania-silica PEG monolith is shown in FIG. 8.

In addition to the ability of extracting polar and moderately polar analytes, the sol-gel germania-silica PEG monolith can also extract nonpolar analytes. Polycyclic aromatic hydrocarbons (PAHs) were extracted on the sol-gel germania PEG monolith with low detection limits, ranging from 3.1 ng/L to 64.4 ng/L. PAHs have different wavelengths for maximum UV absorption. All of these detection limits were determined at 254 nm. It is postulated that the carbon chains within the PEG molecules, which are chemically anchored into the sol-gel germania-silica network, allow the extraction of nonpolar analytes. The HPLC peak area RSD values and detection limit data for PAHs is also given in Table 2. Feng and coworkers (Zheng, et al. *J. Chromatogr. A.* 2007, 1164, 48-55) developed a sol-gel octyl monolith for use in CME hyphenated with HPLC-UV analysis. The sol-gel octyl monolith was capable of extracting PAHs. In that study, the detection limits for fluorene and fluoranthene were 7.1 ng/mL and 8.1 ng/mL, respectively (Fang, et al. *Anal. Chem.* 2007, 79, 9441-9451). The detection limits for fluorene and fluoranthene using the sol-gel-germania PEG monolith are 10.9 ng/L and 8.1 ng/L, respectively. Therefore, in the extraction of these PAHs, the sol-gel germania-silica PEG monolith of the present invention is 743 to 1000 times more sensitive.

The method used for the preparation of the sol-gel germania-silica PEG monoliths was also evaluated in a monolith-to-monolith reproducibility study. Specifically, three sol-gel germania-silica PEG monoliths (30 cm) were prepared independently using the same preparation procedure as described in Example 1. Five compounds, each representative of a different chemical class, were then extracted on the three individually prepared monoliths. The peak area RSD values were calculated for each compound extracted on the three monoliths. For the 5 representative compounds tested, the monolith-to-monolith peak area RSD values ranged from 4.3% to 7.4%. The monolith-to-monolith reproducibility data are presented in Table 3.

TABLE 3

Monolith to monolith peak area reproducibility in CME-HPLC for the sol-gel germania-silica PEG monoliths.

| Chemical Class | Chemical Name | Monolith to Monolith (n = 3) Peak Area RSD (%) |
|---|---|---|
| amine | o-toluidine | 4.3 |
| phenol | 3,5-dimethylphenol | 6.0 |
| alcohol | benzhydrol | 4.6 |
| ketone | trans-chalcone | 6.8 |
| PAH | acenaphthene | 7.4 |

Extraction conditions: 40 cm × 0.32 mm I.D. sol-gel germania-silica PEG monolith Extraction time: 50 min. HPLC conditions: 15 cm × 4.6 mm I.D. Luna $C_{18}$ column; gradient elution 50/50 to 80/20 ACN/water in 10 min; 1 mL/min flow rate, UV detection at 200 nm.

Figure 9A:
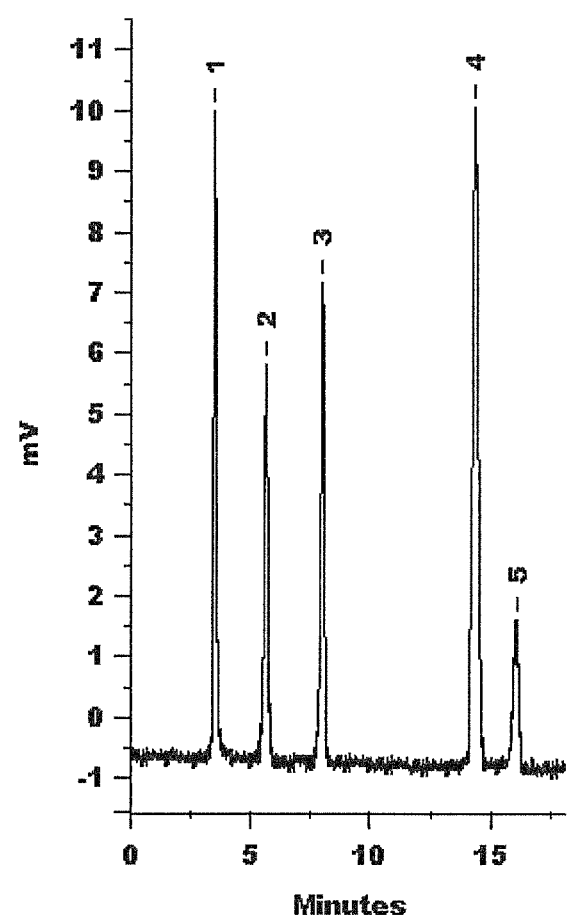
FIGS. 9A-9D show simultaneous CME-HPLC-UV analysis of chemicals from a variety of chemical classes, using the sol-gel germania-silica PEG monolith of the present invention. A before exposure to extreme pH conditions, B after exposure to 1.0 M HCl for 18 h, and C after exposure to 0.1 M NaOH for 18 h, D simultaneous CME-HPLC-UV analysis of the same analytes using a sol-gel germania-silica monolith that does not contain any PEG units. Extraction conditions are: 30 cm×0.32 mm I.D. monolith, 50 mm extraction at room temperature (1 mL/min flow rate). HPLC conditions are: 15 cm×4.6 mm I.D. Luna $C_{18}$ column, gradient elution (45/55 ACN/$H_2O$ for 5 min, then 45/55 to 60/40 ACN/$H_2O$ from 5 to 12 min, 1 ml/min flow rate, UV detection at 200 nm, ambient temperature. 1=m-toluidine ($1\times10^4$ ng/L), 2=3,5-dimethylphenol ($5\times10^4$ ng/L), 3=benzhydrol ($1\times10^4$ ng/L), 4=trans-chalcone ($4\times10^2$ ng/L), 5=acenaphthene ($1\times10^4$ ng/L).

The sol-gel germania-silica PEG coated capillary was capable of simultaneously extracting a mixture of analytes, ranging from polar to nonpolar. The ability to extract these different types of compounds at the same time makes the sol-gel germania-silica PEG monolith suitable for the analysis of complex samples, containing a variety of analytes from different chemical classes. FIG. 9A shows the extraction profiles of samples containing compounds of different chemical classes.

One important advantage of the germania-silica sol-gel materials is the inherent pH stability of germania-based materials, which is superior to that of their silica-based counterparts (Fang, et al. *Anal. Chem.* 2007, 79, 9441-9451). Sol-gel germania-silica PEG monoliths of the present invention were tested for their pH stability by monitoring their extraction capabilities both before and after exposure to highly acidic and highly basic conditions. Five test analytes (m-toluidine, 3,5-dimethylphenol, benzhydrol, trans-chalcone, and acenaphthene), each representative of a different chemical class, were extracted using the sol-gel germania-silica PEG monoliths of the invention.

Figure 9B:
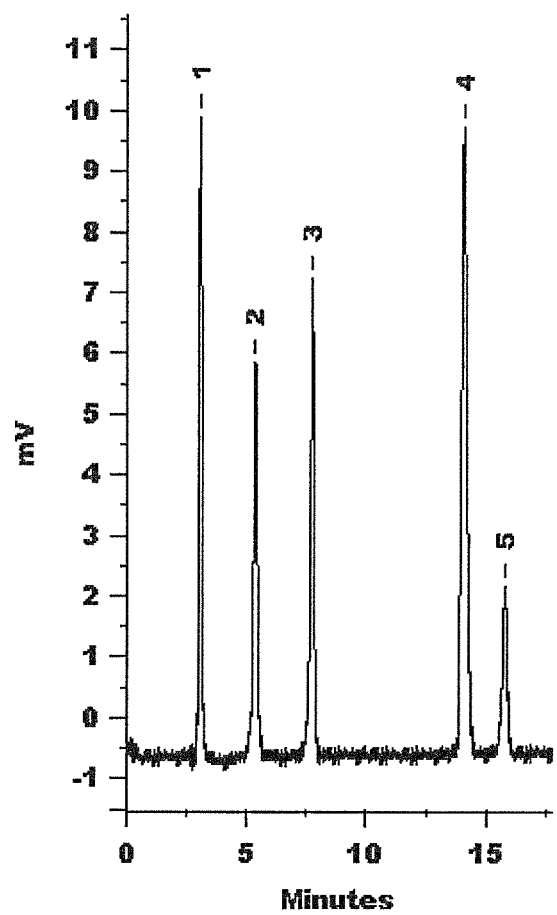

FIG. 9A is a chromatogram depicting the extraction m-toluidine, 3,5-dimethylphenol, benzhydrol, trans-chalcone, and acenaphthene prior to exposing the monolith to extreme pH conditions. After performing this extraction, the sol-gel monolith was exposed to 1.0 M HCl (pH≈0.0) for 18 h. The extraction was repeated, using the same sample of analytes. An HPLC peak area comparison of the analytes both before and after exposing the sol-gel germania-silica PEG monolith to acid is presented in Table 4. The chromatogram of FIG. 9B and the data presented in Table 4 indicate that the acid exposure does not have significantly affect the extraction capabilities of the sol-gel germania-silica PEG monolith.

TABLE 4

HPLC peak area comparison of acids, amines, phenols, alcohols, ketones, and PAHs before and after exposing the sol-gel germania-silica PEG monolith to 1.0M HCl (pH ≈ 0.0) and 0.1M NaOH (pH ≈ 13.0) for 18 h.

| Chemical Class | Chemical Name | Before Exposure Peak Area | After NaOH Exposure Peak Area | After NaOH Exposure % Change | After HCl Exposure Peak Area | After HCl Exposure % Change |
|---|---|---|---|---|---|---|
| Amine | m-toluidine | 6.3 | 6.2 | −1.6 | 6.6 | +4.7 |
| Phenol | 3,5-dimethylphenol | 9.9 | 9.3 | −6.0 | 9.7 | −2.0 |
| Alcohol | benzhydrol | 10.1 | 11.5 | +13.9 | 9.6 | −4.9 |

TABLE 4-continued

HPLC peak area comparison of acids, amines, phenols, alcohols, ketones,
and PAHs before and after exposing the sol-gel germania-silica PEG monolith
to 1.0M HCl (pH ≈ 0.0) and 0.1M NaOH (pH ≈ 13.0) for 18 h.

| Chemical Class | Chemical Name | Before Exposure | After NaOH Exposure | | After HCl Exposure | |
|---|---|---|---|---|---|---|
| | | Peak Area | Peak Area | % Change | Peak Area | % Change |
| Ketone | trans-chalcone | 20.1 | 24.7 | +22.9 | 20.6 | +2.5 |
| PAH | acenaphthene | 5.2 | 8.5 | +63.5 | 5.2 | +0.7 |

Extraction conditions: 30 cm × 0.32 mm I.D. sol-gel germania-silica PEG monolith. Extraction time: 50 min at 1 mL/min flow rate. HPLC conditions: 15 cm × 4.6 mm I.D. Luna $C_{18}$ column; gradient elution 45/55 ACN/water for 5 min to 60/40 ACN/water in 12 min, 1 mL/min flow rate, UV detection at 200 nm, ambient temperature. Peak areas in arbitrary units, average of 3 replicate measurements.

Figure 9C:
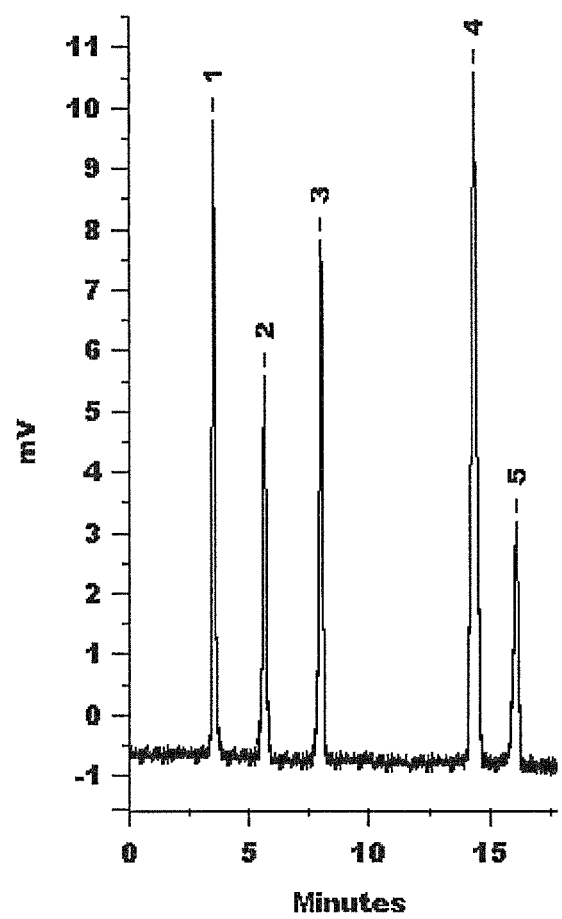
Figure 9D:
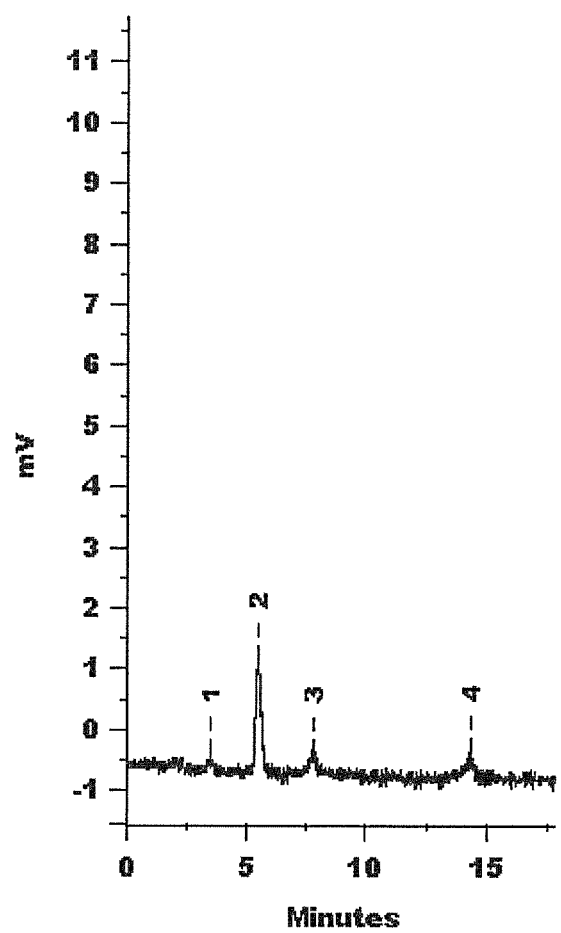

The sol-gel germania-silica PEG monolith was also tested for its stability under highly basic conditions. Specifically, the sol-gel germania-silica PEG monolith was exposed to 0.1 M NaOH (pH≈13.0) for 18 h. Next, the same sample was again extracted on the sol-gel germania-silica PEG monolith, and the results are presented in the chromatogram of FIG. 9C. As shown in the chromatogram and the HPLC peak area comparison in Table 4, the ability of the sol-gel germania-silica PEG monolith to extract amines and phenols did not change significantly after exposure to the base; moreover, its ability to extract alcohols, ketones, and especially PAHs was enhanced. The increased extraction capabilities of the monolith after exposing to acid and base indicate that exposure to harsh pH conditions actually cleans the monolith, opening up more sites for extraction to take place. Upon exposure to stronger base conditions (1.0 M NaOH), the sol-gel germania-silica PEG monolith began to dissolve. This indicates that the sol-gel germania-silica PEG monolith is more resistant to highly acidic conditions than to highly basic conditions. Nevertheless, the sol-gel germania-silica PEG monolith was found to be stable under the pH conditions reported for sol-gel germania PDMS coated microextraction capillaries.

In one embodiment, the sol-gel active organic polymer is polyethylene glycol (PEG). PEG can be used as a porogen in monoliths due to its ability to form strong hydrogen bonds with silanol groups of the growing silicate polymers. Average macropore size and skeleton size is determined by the ratio of PEG/silica ratio and can be adjusted accordingly (Núñez, et al. *J. Chromatogr. A.* 2008, 1191, 231-252). FIG. 9 shows that the sol-gel germania-silica PEG monolith exhibits superior extraction ability when compared to sol-gel germania-silica monolith without PEG under the same conditions. The same sample used in the pH stability tests was extracted on the sol-gel germania-silica PEG monolith, and the resulting chromatogram is presented in FIG. 9D. Only four very small peaks were observed in this chromatogram, indicating that the PEG groups within the sol-gel germania-silica PEG monolith contribute to enhanced extraction capabilities.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] Fang, L.; Kulkarni, S.; Alhooshani, K.; Malik, A. *Anal. Chem.* 2007, 79, 9441-9451

[2] Armelao, L.; Fabrizio, M.; Gross, S.; Martucci, A.; Tondello, E. *J. Mater. Chem.* 2000, 10, 1147-1150.

[3] Majérus, O.; Cormier, L.; Neuville, D. R.; Galoisy, L.; Calas, G. *J. Non-Cryst. Solids.* 2008, 354, 2004-2009.

[4] Winkler, J.; Marme, S. *J. Chromatogr. A.* 2000, 888, 51.

[5] Jiang, Z. T.; Zuo, Y. M. *Anal. Chem.* 2001, 73, 686.

[6] Tani, K.; Suzuki, Y. *J. Chromatogr. A.* 1996, 722, 129.

[7] Tsai, P.; Wu, C. T.; Lee, C. S. *J. Chromatogr. B.* 1994, 657, 285.

[8] Fujimoto, C. *Electrophoresis.* 2002, 23, 2929.

[9] Kim, T. Y.; Alhooshani, K.; Kabir, A.; Fries, D. P.; Malik, A. *J. Chromatogr. A.* 2004, 1047, 165.

[10] Alhooshani, K.; Kim, T. Y.; Kabir, A.; Malik, A. *J. Chromatogr. A.* 2005, 1062, 1.

[11] Chang, C. H.; Gopalan, R.; Lin, Y. S. *J. Membr. Sci.* 1994, 91, 27.

[12] Randon, J.; Huguet, S.; Piram, A.; Puy, G.; Demesmay, C.; Rocca, J.-L. *J. Chromatogr. A.* 2006, 1109, 19.

[13] Hoth, D. C.; Rivera, J. G.; Colón, L. A. *J. Chromatogr. A.* 2005, 1079, 392-396.

[14] O'Dell, L. A.; Gunawidjaja, P. N.; Holland, M. A.; Mountjoy, G.; Pickup, D. M.; Newport, R. J.; Smith, M. E. *Solid State Nuclear Magnetic Resonance.* 2008, 33, 16.

[15] Nawrocki, J.; Dunlap, C.; McCormick, A.; Carr, P. W. *J. Chromatogr. A.* 2004, 1028, 1.

[16] Nawrocki, J.; Dunlap, C.; Li, J.; Zhao, J; McNeff, C. V.; McCormick, A.; Can, P. W. *J. Chromatogr. A.* 2004, 1028, 31.

[17] Claessens, H. A.; Van Sraten, M. A. *J. Chromatogr. A.* 2004, 1060, 23.

[18] Grün, M.; Kurganov, A. A.; Schacht, S.; Schüth, F.; Unger, K. K. *J. Chromatogr. A.* 1996, 740, 1

[19] Liu, M.; Liu, Y.; Zeng, Z. *J. Chromatogr. A.* 2006, 1108, 149-157.

[20] Fujita, K.; Tokudome, Y.; Nakanishi, K.; Miura, K.; Hirao, K. *J. Non-Cryst. Solids.* 2008, 354, 659-664.

[21] Gash, A. E.; Tillotson, T. M.; Satcher, J. H.; Poco, J. F.; Hrubesh, L. W.; Simpson, R. L. *Chem. Mater.* 2001, 13, 999.

[22] Gash, A. E.; Satcher, J. H.; Simpson, R. L. *Chem. Mater.* 2003, 15, 3268.

[23] Gash, A. E.; Tillotson, T. M.; Satcher, J. H.; Hrubesh, L. W.; Simpson, R. L. *J. Non-Cyst. Solids* 2001, 285, 22.

[24] Baumann, T. F.; Gash, A. E.; Chinn, S. C.; Sawvel, A. M.; Maxwell, R. S.; Satcher Jr., J. H. *Chem. Mater.* 2005, 17, 395.

[25] Chen, D. C.; Potter, B. C.; Simmons, J. H. *J. Non-Cryst. Solids.* 1994, 178, 135.

[26] Brusatin, G.; Guglilmi, A.; Martucci, A. *J. Am. Ceram. Soc.* 1997, 80, 3139.

[27] Brede, R.; Danger, T.; Heumann, E; Huber, G.; Chai, B. *Appl. Phy. Lett.* 2000, 63, 729.
[28] McFarlane, R. A. *J. Opt. Soc. Am. B.* (1993) 11, 871.
[29] Downing, E.; Hesselink, J.; Ralston, J.; Macfarlane, R. M. *Science.* 1996, 273, 1185.
[30] Maciel, G. S.; Biswas, A.; Kapoor, R.; Prasad, P. N. *Appl. Phys. Lett.* 2000, 76, 1978.
[31] Shigemura, H.; Kawamoto, H.; Nishii, J.; Takahashi, M.; *J. Appl. Phys.* 1999, 85, 3413.
[32] Que, W.; Wang, L. L.; Chen, T.; Sun, Z.; Hu, X. *Journal of Crystal Growth.* 2006, 288, 75-78.
[33] Rajni, C. H. K. F.; Pita, K.; Ngo, N. Q. *Journal of The Electrochemical Society.* 2005, 152, G456-G459.
[34] Hayes, J. D.; Malik, A. *Anal. Chem.* 2000, 72, 4090-4099.
[35] Wu, R.; Hu, L.; Wang, F.; Ye, M.; Zou, H. *J. Chromatgr. A.* 2008, 1184, 369-392.
[36] Kato, M.; Sakai-Kato, K.; Toyo'oka, T.; Dulay, M. T.; Quirino, J. P.; Bennett, B. D.; Zare, R. N., *J. Chromatgr, A.* 2002, 961, 45-51.
[37] Brinker, C. J.; Scherer, G. W. *Sol-Gel Science: The Physics and Chemistry of Sol-Gel Processing*, Academic Press: San Diego, Calif., 1990, pp 444-99.
[38] Svec, F. *J. Chromatogr. B.* 2006, 841, 52.
[39] Yu, C.; Svec, F.; Frechet, J. M. *Electrophoresis.* 2000, 21, 120.
[40] Rohr, T.; Yu, C.; Davey, M. H.; Svec, F. Frechet, J. M. *J. Electrophoresis.* 2001, 22, 3959.
[41] Yu, C.; Davey, M. H.; Svec, F.; Frechet, J. M. *Anal. Chem.* 2001, 73, 5088.
[42] Yu, C.; Xu, M. C.; Svec, F.; Frechet, J. M. J. *J. Polym. Sci. Part A-Polym. Chem.* 2002, 40, 755.
[43] Núñez, O.; Nakanishi, K.; Tanaka, N. *J. Chromatogr. A.* 2008, 1191, 231-252.
[44] Dulay, M. T.; Quirino, J. P.; Bennett, B. D.; Zare, R. N., *J. Sep. Sci.* 2002, 25, 3.
[45] Shi, Z.; Feng, Y.; Xu, L.; Zhang, M.; Da, S. L. *Talanta.* 2004, 63, 593.
[46] Shi, Z.-G.; Xu, L.-Y.; Feng, Y.-Q. *J. Non-Cryst. Solids.* 2006, 352, 4003-4007.
[47] Hayes, J. D.; Malik, A. *J. Chromatogr. B.* 1997, 695, 3-13.
[48] Legido-Quigley, C.; Marlin, N. D.; Melin, V.; Manz, A.; Smith, N. W.; *Electrophoresis.* 2003, 24, 917-944.
[49] Yang, C. M.; Smatt, J. H.; Zibrowius, B.; Lindén, M. *New J. Chem.* 2004, 28, 1520-1525.
[50] Dulay, M. T.; Quirino, J. P.; Bennet, B. D.; Kato, M.; Zare, R. N. *Anal. Chem.* 2001, 73, 3921-3926.
[51] Zheng, M.; Lin, B.; Feng, Y. *J. Chromatogr. A.* 2007, 1164, 48-55.

What is claimed is:

1. A solid-phase material for extraction of trace analytes in a sample, wherein a surface of the solid-phase material comprises sol-gel germania-silica monolith, wherein the sol-gel germania-silica monolith is formed from sol-gel precursors comprising a germanium alkoxide and/or hydrolyzed germanium alkoxide, an alkoxysilane and/or hydrolyzed alkoxysilane, and a polyglycol.

2. The solid-phase material of claim 1, wherein the germanium alkoxide is tetraethoxygermane, tetramethoxygermane, tetrapropoxygermane, tetrabutoxygermane, or any combination thereof 3. The solid-phase material of claim 1, wherein the alkoxysilane is tetramethoxysilane, trimethoxysilane, triethoxysilane, methyltrimethoxysilane, ethyltrimethoxysilane, n-propyltrimethoxysilane, dimethyldimethoxysilane, diisopropyldimethoxysilane, diisobutyldimethoxysilane, isobutyltrimethoxysilane, n-hexyltrimethoxysilane, n-octyltrimethoxysilane, or any combination thereof.

4. The solid-phase material of claim 1, wherein the polyglycol is polyethylene glycol, methoxypolyethylene glycol, polypropylene glycol, polybutylene glycol, or any combination thereof.

5. The solid-phase material of claim 1, wherein the sol-gel precursors comprise tetraethoxygermane, tetramethoxysilane, and polyethylene glycol.

6. The solid-phase material of claim 1, wherein the solid-phase material further comprises fused silica.

7. The solid-phase material of claim 1, wherein a surface of the solid-phase material is covalently bonded with the sol-gel germania-silica monolith.

8. The solid-phase material of claim 1, wherein the solid phase material forms the stationary phase for microextraction of trace analytes.

9. The solid-phase material of claim 8, wherein the solid phase material is a microextraction capillary and a surface of the inner walls of the capillary is coated with the sol-gel germania-silica monolith.

10. A method of preparing the solid-phase material comprising the sol-gel germania-silica monolith of claim 1 for extraction of trace analytes, comprising:
preparing a sol solution by mixing reagents comprising a germanium alkoxide and/or hydrolyzed germanium alkoxide, an alkoxysilane and/or hydrolyzed alkoxysilane, and a polyglycol, and whereby the sol solution forms into sol-gel germania-silica monolith via polycondensation.

11. The method of claim 10, wherein the reagents further comprise water.

12. The method of claim 10, further comprising mixing the reagents with trifluoracetic acid.

13. The method of claim 12, wherein the sol solution is prepared by mixing the reagents in the following order: a polyglycol, a germanium alkoxide and/or hydrolyzed germanium alkoxide, trifluoracetic acid, and an alkoxysilane and/or hydrolyzed alkoxysilane.

14. The method of claim 10, wherein the solid-phase material is a microextraction capillary, wherein the method further comprises:
a) filling the capillary with the sol solution, whereby forming the sol-gel germania-silica monolith bound to a surface of the inner walls of the capillary; and
b) purging the capillary of unbound sol solution.

15. The method of claim 14, further comprises thermal conditioning the capillary after step (b).

16. The method of claim 10, wherein the reagents comprise tetraethoxygermane, tetramethoxysilane, and polyethylene glycol.

17. A method for extracting, preconcentrating, and/or isolating trace analytes in a sample, comprising:
contacting a sample containing one or more analytes with the column of claim 1; and
desorbing the analytes from the sol-gel germania-silica monolith.

18. The method of 17, wherein the method is performed using capillary microextraction, gas chromatography (GC), capillary electrophoresis, capillary electrochromatography, inductively coupled plasma mass spectrometry, high-performance liquid chromatography (HPLC), or any combination thereof.

19. The method of claim 17, performed at a pH of about 0 or about 14, or at any pH in between 0 and 14.

20. The method of claim 19, wherein the sample comprises a polycyclic aromatic hydrocarbon (PAH), a ketone, an alcohol, a phenol, an amine, or any combination thereof.

* * * * *

UNITED STATES PATENT AND TRADEMARK OFFICE
CERTIFICATE OF CORRECTION

PATENT NO. : 8,603,833 B2
APPLICATION NO. : 13/152720
DATED : December 10, 2013
INVENTOR(S) : Abdul Malik et al.

It is certified that error appears in the above-identified patent and that said Letters Patent is hereby corrected as shown below:

In the Specification

Column 5,
Line 33, "ng/L). FIG. 8" should read --ng/L).
FIG. 8--.
Line 52, "50 mm" should read --50 min--.

Column 9,
Line 41, "(MW-600)" should read --(MW=600)--.
Line 59, "scaled with" should read --sealed with--.

Column 11,
Line 67, "50 mm, and 60 mm." should read --50 min, and 60 min.--.

Column 14,
Line 51, "does not have significantly affect" should read --does not significantly affect--.

Column 15,
Line 67, "9441-9451" should read --9441-9451.--.

Column 16,
Line 44, "Can, P.W." should read --Carr, P.W.--.
Line 49, "740, 1" should read --740, 1.--.
Line 60, "*Non-Cyst.*" should read --*Non-Cryst.*--.

Signed and Sealed this
First Day of July, 2014

Michelle K. Lee
*Deputy Director of the United States Patent and Trademark Office*